(12) United States Patent
Pflughoefft

(10) Patent No.: US 9,782,995 B2
(45) Date of Patent: Oct. 10, 2017

(54) SECURITY AND/OR VALUE DOCUMENT HAVING A TYPE II SEMICONDUCTOR CONTACT SYSTEM

(71) Applicant: Malte Pflughoefft, Berlin (DE)

(72) Inventor: Malte Pflughoefft, Berlin (DE)

(*) Notice: Subject to any disclaimer, the term of this patent is extended or adjusted under 35 U.S.C. 154(b) by 268 days.

(21) Appl. No.: 14/626,682

(22) Filed: Feb. 19, 2015

(65) Prior Publication Data
US 2015/0314630 A1  Nov. 5, 2015

Related U.S. Application Data

(62) Division of application No. 12/377,798, filed on Feb. 17, 2009, now Pat. No. 9,399,365.

(51) Int. Cl.
| | |
|---|---|
| *G06K 9/74* | (2006.01) |
| *B42D 25/378* | (2014.01) |
| *B42D 25/29* | (2014.01) |
| *G01N 21/64* | (2006.01) |
| *B42D 25/36* | (2014.01) |
| *B42D 25/382* | (2014.01) |
| *G07D 7/06* | (2006.01) |

(52) U.S. Cl.
CPC .......... *B42D 25/378* (2014.10); *B42D 25/29* (2014.10); *B42D 25/36* (2014.10); *B42D 25/382* (2014.10); *G01N 21/6408* (2013.01); *G07D 7/06* (2013.01); *B42D 2033/46* (2013.01)

(58) Field of Classification Search
CPC .. B42D 25/387; B42D 25/29; B42D 2033/46; G01N 21/64; G01N 21/6408; G02F 1/035; G06K 7/10; G06K 19/06; B05D 5/06; G01J 3/30; G01J 3/02; G01V 3/08; G01V 3/104; H01L 33/00; B82Y 20/00
See application file for complete search history.

(56) References Cited

U.S. PATENT DOCUMENTS

| | | | |
|---|---|---|---|
| 6,576,155 B1 | 6/2003 | Barbera-Guillem | |
| 6,832,783 B2 | 12/2004 | Lawandy | |
| 7,845,570 B2 | 12/2010 | Schwenk et al. | |
| 2003/0052684 A1* | 3/2003 | Nelson | G01V 3/104 324/329 |
| 2006/0269183 A1* | 11/2006 | Bour | B82Y 20/00 385/2 |
| 2007/0181906 A1* | 8/2007 | Chik | B82Y 20/00 257/103 |
| 2009/0065583 A1* | 3/2009 | McGrew | G01J 3/02 235/454 |

OTHER PUBLICATIONS

GaAs http://www.ioffe.ru/SVA/NSM/Semicond/GaAs/basic.html, 2009.
Heterostructures http://www.ecse.rpi.edu/~schubert/Course-ECSE-6968%20Quantum%20mechanics/Ch17%20Heterostructures.pdf, 2007.
Hybrid Solar Cell http://en.wikipedia.org/wiki/Hybrid_solar_cell, 2009.
Semiconductor Materials http://en.wikipedia.org/wiki/List_of_semiconductor_materials, 2006.

* cited by examiner

*Primary Examiner* — Jamil Ahmed
(74) *Attorney, Agent, or Firm* — Mark Wisnosky

(57) ABSTRACT

The invention relates to a security and/or value document having a security feature, to an ink for making the security feature, to a method for making such a security and/or value document, and to a method for verifying such a security and/or value document.

11 Claims, 3 Drawing Sheets

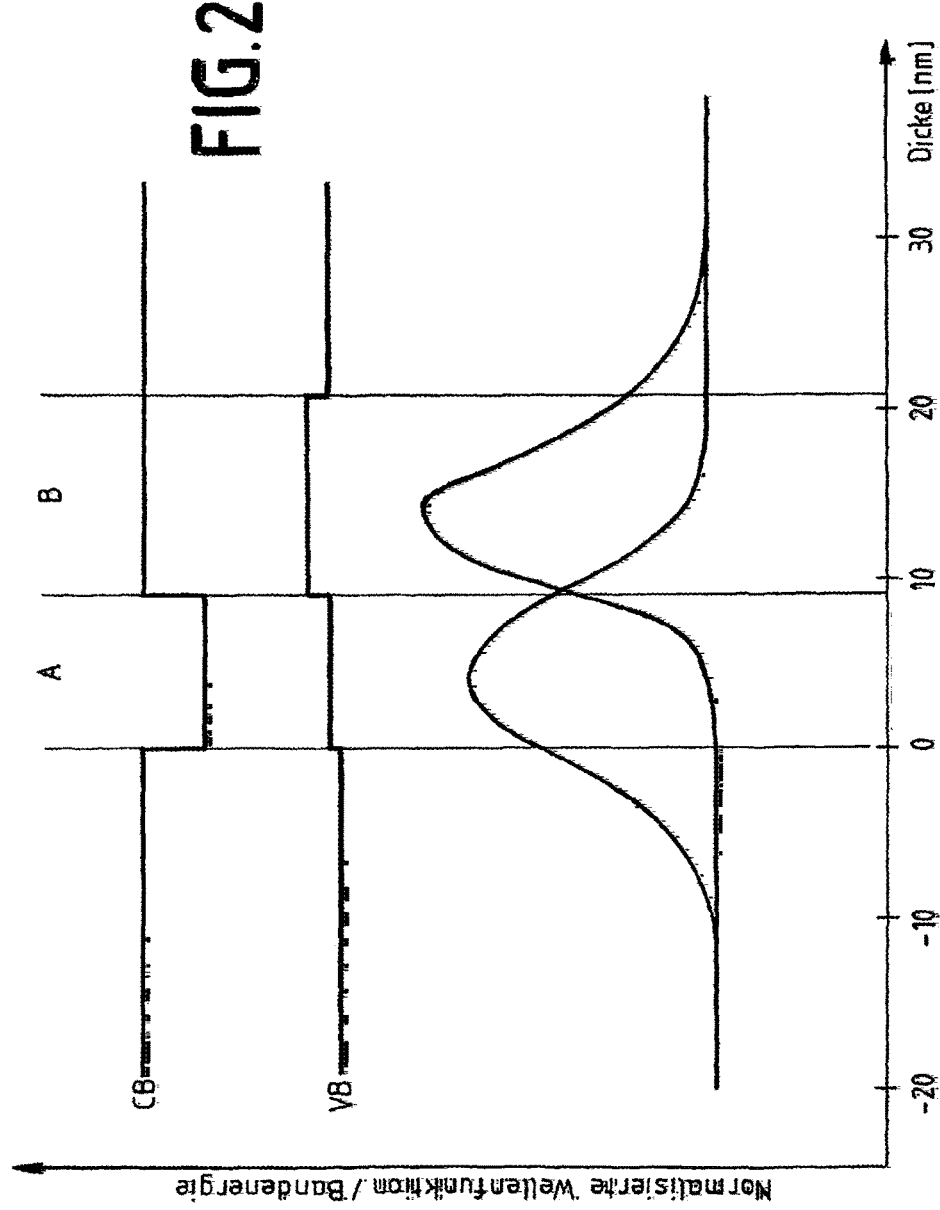

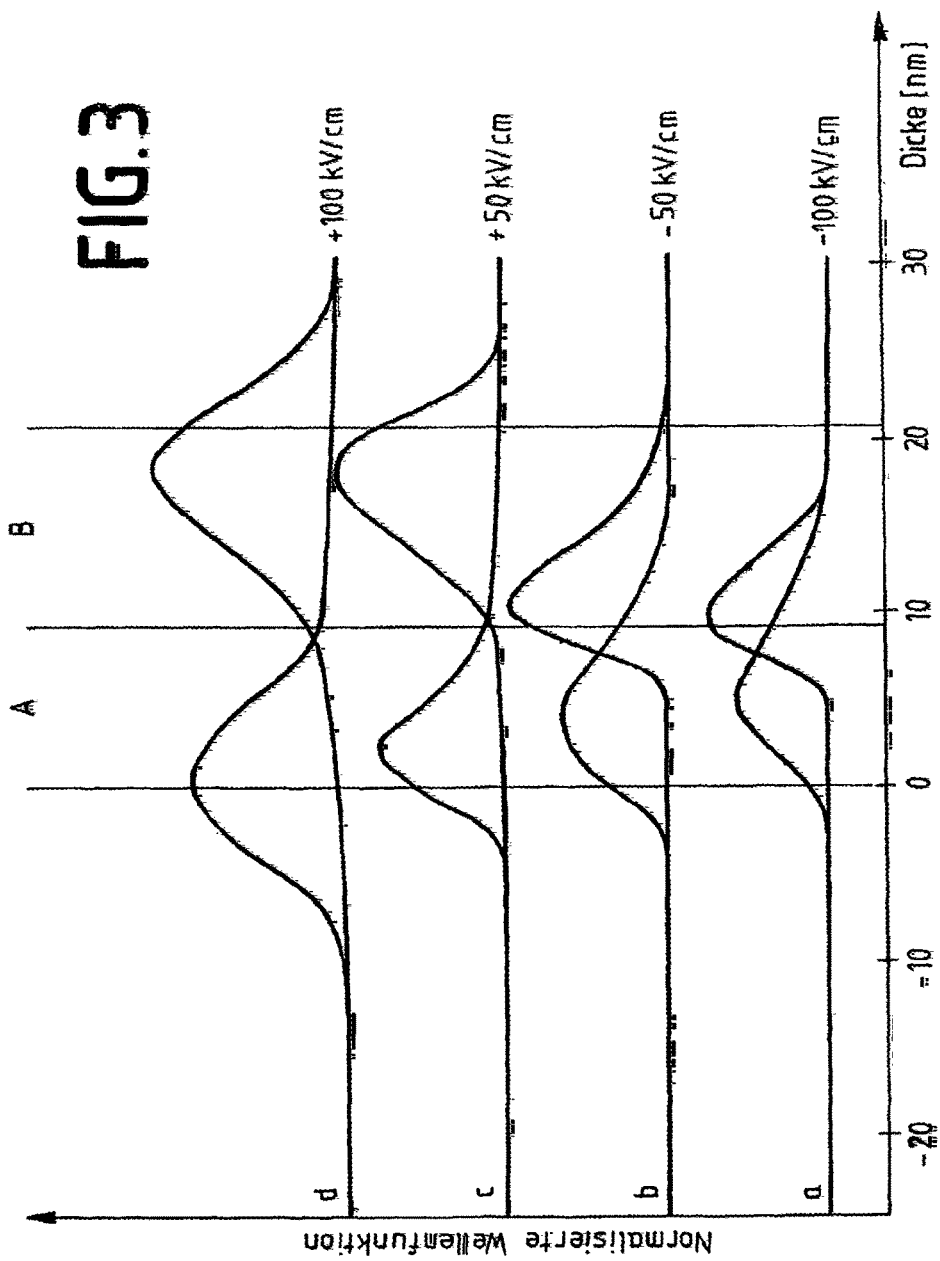

SECURITY AND/OR VALUE DOCUMENT HAVING A TYPE II SEMICONDUCTOR CONTACT SYSTEM

FIELD OF THE INVENTION

The invention relates to a security and/or value document having a security feature, to an ink for making the security feature, to a method for making such a security and/or value document, and to a method for verifying such a security and/or value document.

PRIOR ART AND BACKGROUND OF THE INVENTION

From practical applications, a multiplicity of security and/or value documents are known in the art, which comprise security features with luminescent, in particular fluorescent substances. Luminescent substances are such substances, which fluoresce or phosphoresce upon excitation with light having sufficient energy, for instance UV. These are energetic transition processes on a molecular or atomic level, the transition dipole moment of which is nonzero (fluorescence) or zero (phosphorescence). The wavelengths or energies of the fluorescence or of the phosphorescence are specific for the respective substances, since they correspond to the difference of the energy levels of the two states, between which a relaxation from the excited state takes place, and are in most cases in the visible range. The fluorescence typically has a decay time von 10 ns and less, since it is a dipole allowed transition (nonzero transition dipole moment), whereas the phosphorescence typically has decay times in the range from 1,000 µs up to several hours, since these are dipole forbidden transitions (zero transition dipole moment). Forbidden transitions have a comparably small transition probability, which leads to comparably slow transitions. The physical background of this behavior is for instance described in more detail in the document P. W. Atkins, Physikalische Chemie, 2nd edition, VCH, Weinheim, N.Y., Bale, Cambridge, Tokyo, 1996, pages 563 ff.

In particular, security features with fluorescent substances have the advantage that with simplest means a verification is possible, and that with a very economic production. When such a security feature is for instance held under a UV light source, it will light up and can directly be observed.

Security features with fluorescent substances are usually produced by means of fluorescent paints or inks, for instance by printing. Fluorescent paints or inks are widely used and can easily be procured. Therefore, it is easy for unauthorized persons, too, to procure a suitable fluorescent paint or ink and to make therewith forged security and/or value documents with a fluorescent security feature.

From other technological sectors, in particular the quantum well structures for laser diodes, so-called group II semiconductor contacts are known in the art. Reference is made for instance to the documents J. Am. Chem. Soc. 125: 11466ff (2003), J. Appl. Phys. 87:1304ff (2000), Phys. Rev. B 36:3199ff (1987) and J. Am. Chem. Soc. 125:7100ff (2003). From the document U.S. Pat. No. 5,841,151, various group II semiconductor contacts based on $InAs_xP_y$ and $In_pGa_qAs_xP_y$ are known, and the two mentioned materials are directly contacted with each other and x and y on the one hand and p and q on the other hand always add up to 1. In this document, effects on the wave functions of holes and electrons are also described, which occur upon the application of a potential to the contact. Further similar contacts from two different group III/V semiconductors are for instance known from the document U.S. Pat. No. 6,734,464. From the document L. S. Braginsky et al. "Kinetics of exciton photoluminescence in type-II semiconductor lattices", 2006, decay times of excitons for the system GaAs/AlAs (undoped) and the measurement thereof are known in the art. A detailed background representation of the band structures and wave functions in type II contacts is given further below.

It would be desirable to provide a security and/or value document with a luminescent security feature, which with continued simple production of the security and/or value document offers a higher security against forgery and an improved detectability of forgeries.

TECHNICAL OBJECT OF THE INVENTION

It is therefore the technical object of the invention to provide a security and/or value document, which has a luminescent security feature having a higher security against forgery.

BRIEF DESCRIPTION OF THE DRAWINGS

FIG. 2 shows a normalized wave function/band energy versus Thickness [nm]

FIG. 3 shows a Normalized wave function versus Thickness [nm]

BASICS OF THE INVENTION AND PREFERRED EMBODIMENTS

Figure 1A:
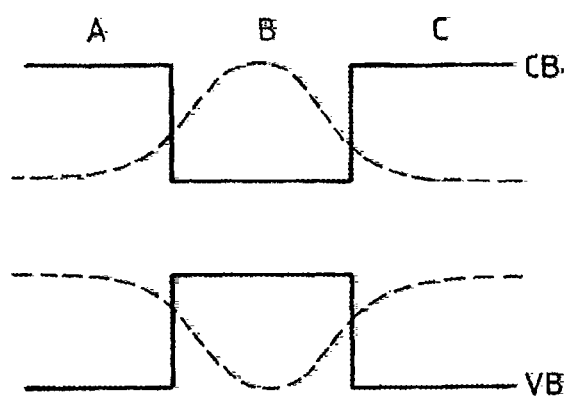
FIG. 1a shows a type I contact between semiconductor materials A and B.

For achieving this technical object, the invention teaches a security and/or value document comprising a security feature with a semiconductor section, which includes at least one first semiconductor layer and one second semiconductor layer, which are contacted with each other and form a type II semiconductor contact system.

The invention is based on the finding that type II semiconductor contacts due to the special physics background generate luminescence, the decay time of which is, by suitable selection and calculation of the materials, in ranges located between those of the classic fluorescence and the phosphorescence. Type II semiconductor contacts are used in other technical sectors, for instance quantum well structures for laser diodes, but there the decay time of the luminescence plays however a less important role, if at all.

By the invention, it is achieved that a security and/or value document according to the invention can still be verified by simple visual observation, but that, by measurement of the decay time of the luminescence, it additionally includes a second inherent and hidden security feature, which can be read out and verified. It is a hidden security feature, since the decay time can only be determined by instruments and cannot be detected by visual observation. If a decay time measured for a security and/or value document to be investigated does not correspond to a reference decay time for the real security feature, the investigated security and/or value document will thus be detected as a forgery and is rejected or confiscated, and that irrespective of the detectable and possibly measurable wavelength of the fluorescence or luminescence. Type II semiconductor contacts cannot easily commercially be obtained, and a forger would have to also perform a suitable selection or calculation of the semiconductor materials, which is simple and usual for a man skilled in the art of solid state physics, does not belong however to the basic knowledge of forgers. Finally, the production of type II semiconductor contacts is expensive, if the required instruments including the operators are not easily available.

A security feature according to the invention is normally adapted such that the semiconductor section or the semiconductor sections form a pattern. Such a pattern may be an identical pattern for different security and/or value documents. Then the pattern is suitable for a verification of a type of security and/or value document. Examples for such document type-specific lateral patterns are: seals, escutcheons, regular or irregular surface patterns such as bands of lines or guilloches, 1D and 2D bar codes. These may be patterns being visible or not visible in normal light, and the not visible patterns differ from the visible patterns by that not visible patterns become only visible by using technical means, such as a UV source. The pattern may however also be an individual pattern for different security and/or value documents (of the same document type), which is coded in particular for identification information of the security and/or value document. For individual patterns, for instance the following data (coded as a pattern) can be employed: alphanumerical sequences of symbols, such as for instance personal data sets, parts of personal data sets, such as name, first name, address, date of birth, place of birth, and/or document data, parts of document data, such as serial number, place of issue, date of issue, date of expiry, and other data, in particular digital data, public key (in the case of a document with readable chip or for access to central or decentralized data banks) and/or check sums, and biometric data, such as photo, finger print, vein pattern for instance of the hand or of a finger, iris and/or retina. Preferably, it is a sequence of symbols identifying in a one-to-one manner the document and/or the document carrier. This sequence of symbols may however also be a sequence of symbols not differently represented in the document. Several patterns may also be provided, which may overlap each other (laterally) and can nevertheless be read out separately, either by the detected luminescence wavelength, or by the measured decay time. Of course, several patterns may also be provided, which do not overlap each other (laterally). In either case, in particular combinations of document type-specific patterns and individual patterns are possible and preferred.

The term value and/or security document comprises for the purpose of the invention in particular identity cards, passports, access allowance cards, visas, control symbols, tickets, driver licenses, vehicle documents, banknotes, checks, postage stamps, credit cards, arbitrary chip cards and adhesive labels (e.g. for product protection). Such security and/or value documents typically comprise a substrate, a printing layer and optionally a transparent cover layer. A substrate is a carrier structure, on which the printing layer with information, pictures, patterns and the like is applied. Materials for a substrate may be all usual materials on a paper and/or plastic basis.

The physical background of the invention is explained in the following. The coefficients of the spontaneous emission (A) and induced absorption (B) are, according to Einstein:

$$A = (8\pi h v^3/c^3) * B \quad \text{Formula 1;}$$

B is further given by:

$$B = \mu_{EA}^2 / (6\epsilon_0 (h/2\pi)^2) \quad \text{Formula 2}$$

Herein, $\mu_{EA}$ is the transition dipole moment of the respective transition, and is given by:

$$\mu_{EA} = -e_0 \text{int}(\Psi^*_E r \ \Psi_A d\tau) \quad \text{Formula 3}$$

Herein, $\Psi$ is the respective wave function of the ground state A and of the excited state E, and r is the spatial coordinate. $d\tau$ is the time differential. "int" is the integral sign. Altogether there results:

$$A = (8\pi h v^3 \mu_{EA}^2) / (6\epsilon_0 (h/2\pi)^2 c^3) \quad \text{Formula 4}$$
$$= ((8\pi h v^3 e_0^2) / (6\epsilon_0 (h/2\pi)^2 /c^3)) * (int(\Psi^*_E r \Psi_A d\ \tau))^2$$

Important for understanding the invention is the above proportionality between A and $(int(\Psi^*_E \ r \ \Psi_A \ d\tau))^2$. In the Formulas, h is Planck's constant, c the speed of light, $\epsilon_0$ the dielectricity constant, $v$ the frequency, and r the distance. If vectors are added or multiplied, this applies to their magnitudes.

The Einstein coefficient of the spontaneous emission is thus in proportion to the square of the overlap integral. If this perception is applied to semiconductor contacts from different semiconductors, then the results shown in FIGS. 1a and 1b will be obtained.

FIG. 1a shows a type I contact between semiconductor materials A and B, and the abscissa is a spatial coordinate and the ordinate is the energy. The full lines show the courses of the conduction band (CB) and of the valence band (VB). It can be seen that in the semiconductor material B the conduction band and the valence band are respectively energy-displaced with a different sign relative to the conduction band and the valence band of the semiconductor material A. The band gap is smallest in the range of the semiconductor B. The wave functions $\Psi$ (broken lines) have in the range of the semiconductor material B, i.e. spatially close to each other, an extreme, so that the overlap integral is at the maximum.

Figure 1B:
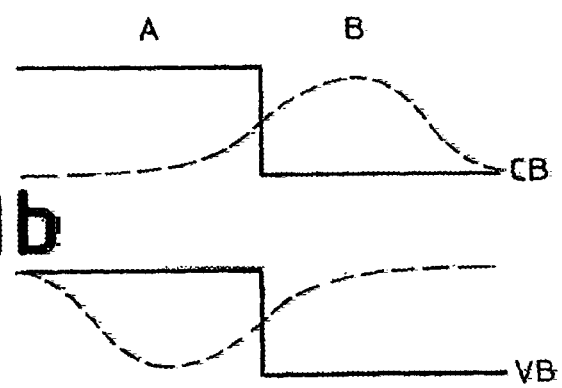
FIG. 1b shows a type II contact between semiconductor materials A and B in an analogous representation.

FIG. 1b shows a type II contact between semiconductor materials A and B in an analogous representation. In the semiconductor material B, here the conduction band and the valence band are respectively energy-displaced with the same sign relative to the conduction band and the valence band of the semiconductor material A. It can be seen that the extremes of the wave functions $\Psi$ are spatially separated from each other, namely on the one hand in the semiconductor material A (GS) and on the other hand in the semiconductor material B (ES), which is characteristic for type II semiconductor contacts. Due to the spatial distance of the wave function extremes, there is a lower probability of the spontaneous emission with the immediate consequence of an extended decay time of the luminescence relative to the semiconductor system with a type I contact.

Figure 1C:
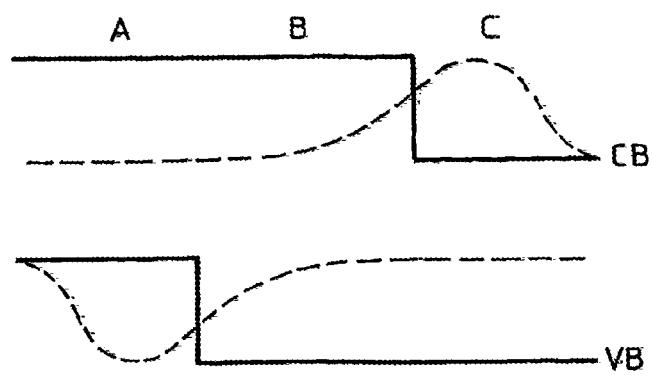
FIG. 1c shows a separating layer C between the semiconductor materials A and B.

These facts can further be enhanced, as shown in FIG. 1c, by that between the semiconductor materials A and B a separating layer C is arranged, and the energy of its conduction band is closer to the conduction band of the semiconductor material A and the energy of its valence band is closer to the valence band of the semiconductor material B. The extremes of the wave functions $\Psi$ are thereby arranged even farer away from each other, so that there is another reduction of the probability of the spontaneous emission and consequently another extension of the decay time.

From the above results that for a type II semiconductor contact system used according to the invention, the decay time can be tailored according to defined guidelines, and that by the selection of the respective band gaps of the two semiconductor materials or of the distances of the respective valence bands and conduction bands to each other and/or by providing a separating layer and by variation of the thickness thereof. A measured decay time is highly specific for the semiconductor material used for a security feature.

Further, by application of a potential between the semiconductor materials A and B so to speak a modulation of the decay time (and also of the emission wavelength) can be achieved. This in addition permits a dynamic verification of the decay time, namely on the one hand without potential and on the other hand with potential, and to use beside the decay time itself also a thus determined difference of decay times for verification. The difference of the decay times will in turn depend on the selected materials for the semiconductor layers and if applicable for the separating layer and be specific therefor. Reference is made to the embodiments.

The term semiconductor section denotes a section of a security and/or value document according to the invention, which is formed by a type II semiconductor contact. In a top view of the security and/or value document, this may be a macroscopic structure, for instance in the order of 1 mm$^2$ and more. Sections are however also microscopic structures, in particular micro or nanoparticles, as described elsewhere.

Such a semiconductor section of a security and/or value document according to the invention can be produced by that A) on a substrate, optionally a first barrier layer is preferably epitaxially grown, B) on the barrier layer, a first semiconductor layer of a first semiconductor material is preferably epitaxially grown, C) optionally on the first semiconductor layer, a separating layer of a separating layer semiconductor material is preferably epitaxially grown, D) on the first semiconductor layer or the separating layer, a second semiconductor layer of a second semiconductor material is preferably epitaxially grown, E) optionally on the second semiconductor layer, a second barrier layer is preferably epitaxially grown, F) optionally the layer structure obtained in steps A) to E) is dissected by division in directions vertically to the planes of the layer structure into particles while maintaining the layer structure, wherein the first semiconductor material and the second semiconductor material are selected and if required doped such that the valence band and the conduction band of the second semiconductor material are respectively energy-displaced with the same sign relative to the valence band and the conduction band of the first semiconductor material, and wherein the separating layer semiconductor material comprises a conduction band, which is energetically closer to the conduction band of the first semiconductor material, and a valence band, which is energetically closer to the valence band of the second semiconductor material, or vice versa.

The production of the layers, in particular of the epitaxial layers can be made in a conventional way. For instance can in particular be used MBE (molecular beam epitaxy) and MOVPE (metal-organic vapor phase epitaxy). These methods with the required instruments, employed substances and deposition conditions according to the composition of a desired semiconductor layer are well known to the man skilled in the art of semiconductor technology and need not be explained here in detail. If applicable, one or several of the semiconductor layers, for instance the barrier layers, may be doped. An n-doped semiconductor is a semiconductor, in which the electrical conduction takes place by electrons due to donor atoms with excess valence electrons. For the n doping of silicon, for instance nitrogen, phosphor, arsenic and antimony can be used. For the n doping of GaP or (AlGa)P semiconductors, for instance silicon and tellurium can be used. In a p-doped semiconductor, the electrical conduction takes place by holes by integration of acceptor atoms. For silicon, acceptors may be boron, aluminum, gallium and indium. For GaP or (AlGa)P, acceptors may for instance be magnesium, zinc or carbon.

Alternatively, particles according to the invention can be synthesized in a dissolved condition following the above documents.

The term contact between the first semiconductor layer and the second semiconductor layer denotes the areal connection of such layers either immediately or under interposition of a separating layer or of several separating layers immediately connected with each other from different separating layer semiconductor materials.

The layer thicknesses of the first and second semiconductor layers and if applicable of the barrier layers are not critical and may be in the range from 0.1 nm to 1 mm, are however preferably between 5 nm and 10 μm. The layer thickness of the separating layer or the sum of the thicknesses of several separating layers should however be rather small, and should be in the range from 0.1 to 100 nm, preferably in the range from 0.5 to 50 nm, in particular in the range from 0.5 to 20 nm.

For the purpose of the invention, the semiconductor section can be configured in most different manners.

In a particularly simple variant of the invention, semiconductor sections are adapted as semiconductor particles, which are arranged in the security and/or value document or at the surface thereof. The particles are in the simplest embodiment not electrically contacted, electroluminescence cannot take place. This may occur by integration in a substrate, for instance of paper or plastic, in a printing layer provided on the substrate, for instance using an ink, and/or in a cover layer provided on the printing layer, for instance of a transparent plastic. It is technologically particularly preferred, if a multiplicity of semiconductor particles are arranged or mixed in a printing ink applied in or on the security and/or value document, since then the complete production process differs from conventional production processes only by that an ink supplemented with the semiconductor particles according to the invention is processed. This variant of the invention can be used for practically all security and/or value documents in question.

A technologically more expensive variant is characterized by that the semiconductor section comprises electrical contacts, which are connected on the one hand with the first semiconductor layer and on the other hand with the second semiconductor layer, for instance by means of the barrier layers, wherein the electrical contacts are electrically connected respectively with electrical contact fields, which are arranged in the area of the surface of the security and/or value document. Thus, by application of a potential, the above modulation of the decay time can be performed. This variant is recommended mainly for security and/or value documents, which anyway comprise a contact field, for instance for a chip, such as chip cards, identification cards, passports and the like. Instead of electrical contacts, conductive layers representing a capacitor may also be provided, and reference is in detail made to the following description. In this variant, the contact fields are typically not intended for the excitation of electroluminescence, or electroluminescence does not occur upon application of a potential difference.

A semiconductor section typically used for the purpose of the invention has a decay time of the luminescence from 1 to 100,000 ns, preferably from 10 to 10,000 ns. The decay time is the time, which elapses between the initial intensity of the luminescence immediately after the end of the excitation and the drop of the intensity of the luminescence to 1/e of the initial intensity. Alternatively, the decay time may also be the time of the drop to 1/10 of the initial intensity; both values differ by a factor of approx. 2.3. The decay time can be measured either selectively for a defined wavelength, or in a non-wavelength selective manner.

For the purpose of the invention, the first semiconductor layer and the second semiconductor layer may in principle be made from arbitrary semiconductor materials, if applicable doped, wherein the selection and composition is made such that a type II semiconductor contact is formed. In particular, all type II semiconductor contacts are suitable, which are known from the technological sector of the quantum well structures in manifold variants. The layers of these contacts are in most cases formed by groups III/V or II/VI semiconductors. As group III elements, B, Al and In can also be used, beside Ga. As group V elements, N, P and Sb can also be used, beside As. Often, different elements of the respective groups are used in a layer, and thereby desired band structures of the layers can also be modeled by variation of the stoichiometry of different group III elements on the one hand and/or different group V elements on the other hand, reference being made to the technical literature for groups III/V semiconductors. Analog considerations apply to the components of the separating layer and/or of the barrier layer(s), wherein a barrier layer can in principle fulfill the same function as in quantum well structures and may further also be conductive, for instance by doping, and thus also serve for an electrical contacting.

The invention further relates to an ink for imprinting a substrate of a security and/or value document comprising particles with at least two semiconductor layers, which form a type II semiconductor contact system. The other components of inks according to the invention correspond to the components of inks known from prior art and typically comprise the other conventional components of paints or inks, such as binding agents, penetration agents, preservation agents, biocides, tensides, buffer substances, solvents (water and/or organic solvents), filling materials, pigments, dyes, effect pigments, anti-foam agents, anti-deposition agents, UV stabilizers, etc. Suitable paint and ink formulations for different printing methods are well known to the average man skilled in the art, and particles used according to the invention insofar are added in lieu of or in addition to conventional dyes or pigments. The proportion of the particles in the ink may be in the range from 0.01 to 50 wt. %, preferably from 0.01 to 10 wt. %, most preferably from 0.1 to 2 wt. %, with regard to the total weight of the ink. The particles may have a maximum spatial extension from 0.001 to 100 μm, preferably from 0.01 to 20 μm, in the case of ink-jet inks from 0.001 to 0.1 μm or 1 μm. The maximum spatial extension denotes the length of the straight connection between two points of the surface of a particle, which is maximum for the particle.

Suitable printing methods for applying the printing layer with an ink according to the invention on the substrate are the methods being well known to the man skilled in the art, namely the gravure, letterpress, flat screen, and silk screen printing. For instance may be used: recess, photogravure, flexo, letterset, offset or serigraphy printing. Further, digital printing methods are suitable, such as thermotransfer, ink jet or thermosublimation printing.

The invention further relates to a method for making a security and/or value document according to the invention, wherein a semiconductor section, which comprises at least one first semiconductor layer and one second semiconductor layer, which form a type II semiconductor contact system, is introduced into a substrate of the security and/or value document or is applied on the surface thereof, and wherein the first semiconductor layer is electrically contacted with a first electrical contact field and wherein the second semiconductor layer is electrically contacted with a second electrical contact field. In the simplest case, the substrate of the security and/or value document is imprinted with an ink according to the invention.

Generally, the invention in the embodiment with potential difference application between the first semiconductor layer and the second semiconductor layer may alternatively be configured such that instead of contacting the said semiconductor layers, these are arranged between two layers being electrically conductive and electrically isolated relative to the semiconductor layers. These electrically conductive layers are then respectively contacted with the electrical contact fields. Thereby, a capacitor is formed, in the field of which (upon application of a potential difference to the two electrically conductive layers) the semiconductor layers are located and consequently corresponding fields are generated at the boundary layer between the semiconductor layers.

The invention further relates to a method for verifying a security and/or value document according to the invention, wherein the security and/or value document is irradiated with a light radiation, the energy of which is sufficient for the excitation of the luminescence of the semiconductor section, wherein the decay time of the excited luminescence is measured and compared to a first reference decay time value. Measurements of the decay time can be made with conventional devices, and reference is exemplarily made to the embodiments.

In an improvement of the above method for verifying the security and/or value document with an electrically contacted semiconductor section, a defined potential difference is applied to the first electrical contact field and the second electrical contact field, wherein the security and/or value document is irradiated with a light radiation, the energy of which is sufficient for the excitation of the luminescence of the semiconductor section, and wherein the decay time of the excited luminescence is measured and compared to a second reference decay time value. Suitable are potential differences, which generate in the area of the contact field strengths in the range from 0.1 to 100,000 or 10,000 kV/cm, preferably 5 to 200 kV/cm. In addition, the decay time of the excited luminescence can be measured without application of a potential difference, wherein the difference of the measured decay times without and with application of the potential is compared to a reference decay time difference value. The potential difference to be applied is defined and the value thereof is assigned to the security feature and if applicable to the reference decay time difference value. The measurement of the decay time can be repeated for different potential differences, in order to increase the security of the verification.

For the purpose of the invention, the excitation of the luminescence cannot only be made with a radiation, the energy of which is equal to or greater than the energy difference of the two luminescence states, but also with a radiation, the energy of which is smaller than this energy difference. Then the excitation can be achieved by two or more-photon excitation or upconversion in a conventional manner.

In the following, the invention is explained in more detail with reference to embodiments representing examples only.

Example 1: A Type II Semiconductor Contact Used According to the Invention

A first semiconductor layer A is made from $InAs_{0.43}P_{0.57}$ in a thickness of 9.0 nm (the stoichiometric indexes of the group III and group V elements add up to 1). It is a layer for electrons. The band energy of the conduction band is −8.295 eV. The band energy for heavy holes in the valence band is −9.220 eV. The band energy for light holes in the valence band is −9.307 eV.

A second semiconductor layer is made from $In_{0.53}Ga_{0.47}As_{0.71}P_{0.29}$ in a thickness von 12.0 nm. It is a layer for holes. The band energy of the conduction band is −8.169 eV. The band energy for heavy holes is −9.178 eV. The band energy for light holes is −9.105 eV.

On either side of the above structure, barrier layers of $In_{0.73}Ga_{0.27}As_{0.49}P_{0.51}$ with a thickness of 30 nm are provided. The band energy of the conduction band is −8.173 eV. The band energy for heavy holes is −9.228 eV. The band energy for light holes is −9.206 eV.

FIG. 2 shows a diagrammatic representation of the normalized wave functions Ψ. It can be seen that the respective extremes are spatially separated, which leads to a decay time being extended relative to the luminescence in type I contacts.

Example 2: Modification of the Decay Time by Application of a Potential to the Type II Contact from Example 1

In FIG. 3 are shown the normalized wave functions Ψ, as given by the application of potentials, in fields in the contact region of −100 kV/cm (a), −50 kV/cm (b), +50 kV/cm (c) and +100 kV/cm (d). It can be seen that the spatial separation of the maxima varies and can be controlled with the field strength and thus with the applied potential, with the consequence that the decay times, too, are variable and controllable. To a defined field strength or potential difference, a specific displacement of the decay time can be assigned.

Example 3: Measurement of Decay Times for the Type II Contact GaAs/AlAs

The decay times of the luminescence for a type II contact system of undoped GaAs and AlAs (without separating layer) are investigated. $X_Z$ excitons are excited with a YAG:Nd pulse laser with a wavelength of 532 nm and a pulse duration of 15 µs. $X_{XY}$ excitons are excited with a $N_2$ laser with a wavelength of 337 nm and a pulse duration of 0.15 µs. The luminescence is measured by means of a double grating monochromator with a photomultiplier as detector. The decay time measurements or lifetime measurements are performed by means of the time-correlated single-photon counting technique. The intensity of the luminescence due to the $X_Z$ excitons drops within approx. 5.5 µs to ¹/₁₀ of the initial intensity. The intensity of the $X_{XY}$ excitons drops within approx. 950 µs to ¹/₁₀ of the initial intensity.

In a corresponding manner, the decay times can be measured under application of a potential between the GaAs and the AlAs layers, wherein then an increase or a reduction of the decay times, depending on the polarity and size of the potential, can be detected. Then it is also possible to determine the difference of the decay times with and without applying a potential.

Example 4: Production of an Ink According to the Invention

For ink-jet printing of a security feature in red paint in a passport, the following components are mixed and homogenized:
20.0 wt. % of Cartasol Red K-3B liquid,
40.6 wt. % of lactic acid (80%),
19.6 wt. % of ethandiol (ethylene glycol),
1.6 wt. % of water,
16.7 wt. % of ethylene glycol-monobutyl ether,
0.2 wt. % of Parmetol A26,
1.3 wt. % of sodium lactate solution (50%).

The total amount of water under consideration of the water brought in with the Cartasol is 30 wt. %, referred to the total amount of ink. By using Cartasol, further 1 wt. % of acetic acid, referred to the total amount of ink, is comprised.

To the thus produced conventional ink, 0.1 wt. %, with regard to the total amount of ink, of particles with a maximum spatial extension of 0.1 µm with a type II semiconductor contact according to Example 1 are added, and the ink is homogenized.

Example 5: Verification of a Security and/or Value Document According to the Invention A security and/or value document comprising a security feature with semiconductor sections according to the invention, for instance as particles for the purpose of imprinting with an ink according to Example 4, is irradiated with a UV excitation radiation and subjected to a decay time measurement in an analogous manner to Example 3. The measured decay time is compared to a reference decay time, which was measured before at a reference security feature. When a difference of the measured decay time and the reference decay time exceeds a defined admissible deviation window (which is substantially determined by the measuring error tolerances of the used instruments), the security and/or value document is qualified as forged and is confiscated.

Example 6: Verification of Another Security and/or Value Document According to the Invention A security and/or value document, which comprises a security feature with a type II semiconductor contact used according to the invention, wherein the semiconductor materials of the semiconductor contact are connected respectively with electrical contact fields, is irradiated with a UV excitation radiation and the decay time is measured. Then a voltage is applied to the electrical contact fields, for instance 0.5 V, and the measurement of the decay time is repeated.

First, a comparison of the decay time is performed without voltage with the reference decay time according to Example 5. Then the decay times of the two measurements are subtracted from each other, and the obtained difference of the measured decay times is compared to a reference difference in an analogous manner to the above comparison.

When a difference of the measured decay time and the reference decay time exceeds a defined admissible deviation window and/or when the difference of the difference of the measured decay times and the reference decay time exceeds a defined second admissible deviation window, the security and/or value document is qualified as forged and is confiscated.

What is claimed is:
1. A method for verifying authenticity of a security and/or value document, said document comprising a security feature with a semiconductor section, which comprises at least one first semiconductor layer and one second semiconductor layer, which are contacted with each other and form a type II semiconductor contact system, wherein the first semiconductor layer is comprised of $InAs_{0.43}P_{0.57}$ and the second semiconductor layer is comprised of $In_{0.53}Ga_{0.47}As_{0.71}P_{0.29}$, and electrical contacts connected with the first and second semiconductor layers respectively with electrical contact fields, said method comprising:
  a. irradiating the document with a light radiation, the energy of the light radiation is at least one selected from:
    i. energy sufficient for the excitation of the luminescence of the semiconductor section, and,
    ii. energy which is suitable for the excitation of the luminescence by two or more-photon processes and upconversion, and,
  b. measuring a first decay time of the excited luminescence, and,
  c. comparing the measured first decay time to a first reference decay time value, and,
  d. if the difference between the measured first decay time and the first reference decay time is less than a pre-selected value verifying that the document is authentic, and,
  e. if the difference between the measured first decay time and the first reference decay time is greater than a pre-selected value verifying that the document is not authentic.

2. The method of claim 1 wherein the first reference decay time is determined by measuring the decay time of excited luminescence at a time after applying the security feature to a known authentic document.

3. The method according to claim 1 further including:
  a. applying a pre-selected potential difference between the electrical contact field of the first semiconductor layer and the electrical contact field of the second semiconductor layer, and,
  b. irradiating the security and/or value document with a light radiation, the energy of which is at least one selected from:
    i. energy sufficient for the excitation of the luminescence of the semiconductor section, and,
    ii. energy which is suitable for the excitation of the luminescence by two or more-photon processes and upconversion, and,
  c. measuring a second measured decay time of the excited luminescence while applying the pre-selected potential difference, and,
  d. comparing the second measured decay time to a second reference decay time value and if the difference between the second measured decay time and the second reference decay time is less than a pre-selected value verifying that the document is authentic, and,
  e. if the difference between the second measured decay time and the second reference decay time is greater than a pre-selected value verifying that the document is not authentic.

4. The method of claim 3 further including:
  a. comparing a first difference of the first and second measured decay times with a second difference of the first and second reference decay times, and,
  b. if the difference between the first difference and the second difference is greater than a pre-selected value verifying that the document is not authentic.

5. The method of claim 3 wherein the wherein the second reference decay time is determined by measuring the decay time of excited luminescence at the first time after applying the security feature to a known authentic document and while applying the pre-selected potential difference to the electrical contacts.

6. A method of verifying the authenticity of a security and/or value document with a semiconductor section said method comprising:
  a. applying a first semiconductor layer to a substrate,
  b. applying a second semiconductor layer to the first semiconductor layer thereby forming a type II semiconductor contact system,
  c. applying a first electrical contact to the first semiconductor layer and a second electrical contact to the second semiconductor layer, said first and second electrical contacts isolated from one another, and,
  d. applying the type II semiconductor contact system with the electrical contacts to at least one authentic security and/or value document,
  e. irradiating at least one of the at least one authentic security and/or value document with a light radiation, the energy of which is at least one selected from:
    i. energy sufficient for the excitation of the luminescence of the semiconductor section, and,
    ii. energy which is suitable for the excitation of the luminescence by two or more-photon processes and upconversion, and,
  f. measuring a first reference decay time of the excited luminescence from the irradiating at least one of the at least one authentic security and/or value document, and,
  g. measuring a second reference decay time of the excited luminescence from the irradiating at least one of the at least one authentic security and/or value documents while applying a preselected potential difference to the electrical contacts, and,
  h. irradiating at least one security and/or value document said document's authenticity to be verified, with light radiation, the energy of which is the same as used to measure the first reference decay time, and,
  i. measuring a first measured decay time of an excited luminescence from the irradiating the at least one security and/or value document to be verified, and,
  j. measuring a second measured decay time of an excited luminescence from the irradiating the at least one security and/or value document to be verified, and,
  k. comparing the first measured decay time with the first reference decay time, and,
  l. if the difference between the first measured decay time and the first reference decay time is less than a pre-selected value verifying that the document to be verified is authentic, and,
  m. if the difference between the first measured decay time and the first reference decay time is greater than a pre-selected value verifying that the document to be verified is not authentic.

7. The method according to claim 6 further including:
  a. applying a first potential difference to the electrical contacts, and,
  b. irradiating at least one of the at least one authentic security and/or value documents with a light radiation, the energy of which is at least one selected from:
    i. energy sufficient for the excitation of the luminescence of the semiconductor section, and,
    ii. energy which is suitable for the excitation of the luminescence by two or more-photon processes and upconversion, and,
  c. measuring a second reference decay time of the excited luminescence while applying the first potential difference, and, d. irradiating the at least one security and/or value document to be verified with a light radiation, the energy of which is the same as used to measure the second reference decay time, and,
e. measuring a second measured decay time of the excited luminescence from the irradiating the at least one security and/or value document to be verified while applying the first potential difference, and,
f. computing a first difference of the first reference decay times and the second reference decay time, and,
g. computing a second difference of the first measured decay time and the second measured decay time, and,
h. comparing the first difference and the second difference and if the difference of the first and second difference is less than a preselected value verifying the document to be verified as authentic, and,
i. if the difference of the first and second difference is greater than a preselected value verifying that the document to be verified is not authentic.

8. The method of claim 7 wherein the first semiconductor layer is comprised of $InAs_{0.43}P_{0.57}$ and the second semiconductor layer is comprised of $In_{0.53}Ga_{0.47}As_{0.71}P_{0.29}$.

9. A method of verifying the authenticity of a security and/or value document with a semiconductor section said method comprising:
a. applying a first barrier layer to a substrate,
b. applying a first semiconductor layer to the first barrier layer,
c. applying a second semiconductor layer to the first semiconductor layer thereby forming a type II semiconductor contact system,
d. applying a second barrier layer to the second semiconductor layer, and,
e. applying a first electrical contact to the first semiconductor layer and a second electrical contact to the first and second barrier layers respectively, thereby forming a capacitor in the field of which is located the type II semiconductor contact system, and,
f. applying the type II semiconductor contact system with the electrical contacts to at least one authentic security and/or value document,
g. irradiating at least one of the at least one authentic security and/or value document with a light radiation, the energy of which is at least one selected from:
  i. energy sufficient for the excitation of the luminescence of the semiconductor section, and,
  ii. energy which is suitable for the excitation of the luminescence by two or more-photon processes and upconversion, and,
h. measuring a first reference decay time of the excited luminescence from the irradiating at least one of the at least one authentic security and/or value document, and,
i. irradiating at least one security and/or value document said document's authenticity to be verified, with light radiation, the energy of which is the same as used to measure the first reference decay time, and,
j. measuring a first measured decay time of an excited luminescence from the irradiating the at least one security and/or value document to be verified, and,
k. comparing the first measured decay time with the first reference decay time, and,
l. if the difference between the first measured decay time and the first reference decay time is less than a pre-selected value verifying that the document to be verified is authentic, and,
m. if the difference between the first measured decay time and the first reference decay time is greater than a pre-selected value verifying that the document to be verified is not authentic.

10. The method according to claim 9 further including:
a. applying a first potential difference to the electrical contacts, and,
b. irradiating at least one of the at least one authentic security and/or value documents with a light radiation, the energy of which is at least one selected from:
  i. energy sufficient for the excitation of the luminescence of the semiconductor section, and,
  ii. energy which is suitable for the excitation of the luminescence by two or more-photon processes and upconversion, and,
c. measuring a second reference decay time of the excited luminescence while applying the first potential difference, and,
d. irradiating the at least one security and/or value document to be verified with a light radiation, the energy of which is the same as used to measure the second reference decay time, and,
e. measuring a second measured decay time of the excited luminescence from the irradiating the at least one security and/or value document to be verified while applying the first potential difference, and,
f. computing a first difference of the first reference decay times and the second reference decay time, and,
g. computing a second difference of the first measured decay time and the second measured decay time, and,
h. comparing the first difference and the second difference and if the difference of the first and second difference is less than a preselected value verifying the document to be verified as authentic, and,
i. if the difference of the first and second difference is greater than a preselected value verifying that the document to be verified is not authentic.

11. The method of claim 9 wherein the first semiconductor layer is comprised of $InAs_{0.43}P_{0.57}$ and the second semiconductor layer is comprised of $In_{0.53}Ga_{0.47}As_{0.71}P_{0.29}$ and the barrier layers are comprised of $In_{0.73}Ga_{0.27}As_{0.49}P_{0.51}$.

* * * * *